United States Patent [19]

Trofast et al.

[11] Patent Number: 5,549,101
[45] Date of Patent: Aug. 27, 1996

[54] DOSAGE INHALATOR WITH INDICATING/INTERRUPTING MEANS

[75] Inventors: Eva A. Trofast, Lund; Kjell I. L. Wetterlin, Södra Sandby, both of Sweden; Risto K. V. Virtanen, Nurmijärvi, Finland

[73] Assignee: Astra Aktiebolag, Sodertalje, Sweden

[21] Appl. No.: 331,589

[22] PCT Filed: May 4, 1993

[86] PCT No.: PCT/SE93/00389

§ 371 Date: Nov. 14, 1994

§ 102(e) Date: Nov. 14, 1994

[87] PCT Pub. No.: WO93/21980

PCT Pub. Date: Nov. 11, 1993

[30] Foreign Application Priority Data

May 5, 1992 [SE] Sweden .................................. 01411

[51] Int. Cl.⁶ .................................................. A61M 15/00
[52] U.S. Cl. ................. 128/203.15; 128/203.12; 128/203.21; 128/205.23; 128/200.14; 604/58
[58] Field of Search ............... 128/200.14, 200.23, 128/203.23, 203.24, 203.29, 204.23, 205.23, 200.24, 203.25, 203.15, 203.12, 200.12, 203.21; 604/58

[56] References Cited

U.S. PATENT DOCUMENTS 4,524,769  6/1985  Wetterlin .
4,668,218  5/1987  Virtanen .
4,817,822  4/1989  Rand et al. ................. 128/200.14
5,033,463  7/1991  Cocozza ...................... 128/203.21

FOREIGN PATENT DOCUMENTS 0645986   4/1991  Australia ................. 128/203.12
2041763   9/1980  United Kingdom .
9113646   9/1991  United Kingdom .............. 604/58
WO91/12040  8/1991  WIPO .
WO92/00771  1/1992  WIPO .

*Primary Examiner*—Edgar S. Burr
*Assistant Examiner*—V. Srivastava
*Attorney, Agent, or Firm*—Fish & Richardson P.C.

[57] ABSTRACT

A dosage inhalator is provided for dispensing to a patient a pharmacologically active compound suspended in a fluid. The dosage inhalator includes a carrier having portions for carrying, by intermittent movement, predetermined and reproducible unit doses of the active compound to a conduit through which it is delivered; a maneuverer for actuating the intermittent movement of the carrier, the maneuverer being movable between first and second predetermined positions by a user of the inhalator; and a member for disrupting the movement of the maneuverer upon exhaustion of the active compound in the storage means. The carrier is actuated by a ratchet mechanism including a spring-biased pawl, the maneuverer includes a lever that is reciprocally displaceable between two distinct positions, and the movement of the ratchet mechanism is limited by the displacement of the lever.

17 Claims, 2 Drawing Sheets

DOSAGE INHALATOR WITH INDICATING/INTERRUPTING MEANS

TECHNICAL FIELD OF THE INVENTION

The present invention relates to a dosage inhalator for dispensing to a patient a pharmacologically active compound or substance suspended in a fluid comprising a nozzle, a conduit connected to said nozzle, a storage means adjacent said conduit containing multiple doses of said active compound to be dispensed, a carrying means having portions for carrying predetermined and reproducible unit doses of said active compound, said carrying means being mounted for movement between said conduit and said storage means to position one of said portions in said conduit whereby said unit dose of said active compound located at said portion can be dispensed into the conduit said carrying menas being actuated by means of a maneuvering means.

BACKGROUND OF THE INVENTION

Dosage inhalators of the general type described above are disclosed for instance in U.S. Pat. No. 4,524,769, which is directed towards a dosing means in a dosage inhalator, and U.S. Pat. No. 4,668,218, which is directed towards a indicating means indicating the number of doses used or still remaining in a dosage dispensing means illustrated in an inhalator. In some cases it may however be advantageous that the patient is given a clear and unambiguous indication that the supply of the pharmacologically active compound is exhausted. It further is desirable with an indicating means having a design which is simple and cheap to manufacture and which in a simple way can be set automatically to the actual number of doses filled into the dosage inhalator.

SUMMARY OF THE INVENTION

These and other objects are achieved in that said inhalator comprises means for disrupting the movement of said maneuvering means directly or indirectly upon exhaustion of said active compound in said storage means. In this description the expression "disrupt" is used in the sense "to cause to break down", for instance locking the maneuvering means or allowing the maneuvering means to rotate freely in one or both rotational directions. In this way the patient is given a clear indication that the supply of compound is exhausted.

A further aspect of said inhalator is the providing of means for indicating either the number of doses remaining in said storage means or the number of doses used, said indicating means comprising a screw and nut mechanism being rotated by said intermittent movement of said carrying means, the relative movement between the screw and the nut in said mechanism being caused by said rotation being used for actuating said indicating means. The screw and nut mechanism preferably is provided with features for a quick adjustment in order to allow the indicating means to be preset easily to different numbers of doses.

In a preferred embodiment the relative movement between the screw and the nut in the screw and nut mechanism is utilized to disrupt the movement of the maneuvering means.

DETAILED DESCRIPTION OF PREFERRED EMBODIMENTS

Figure 2:
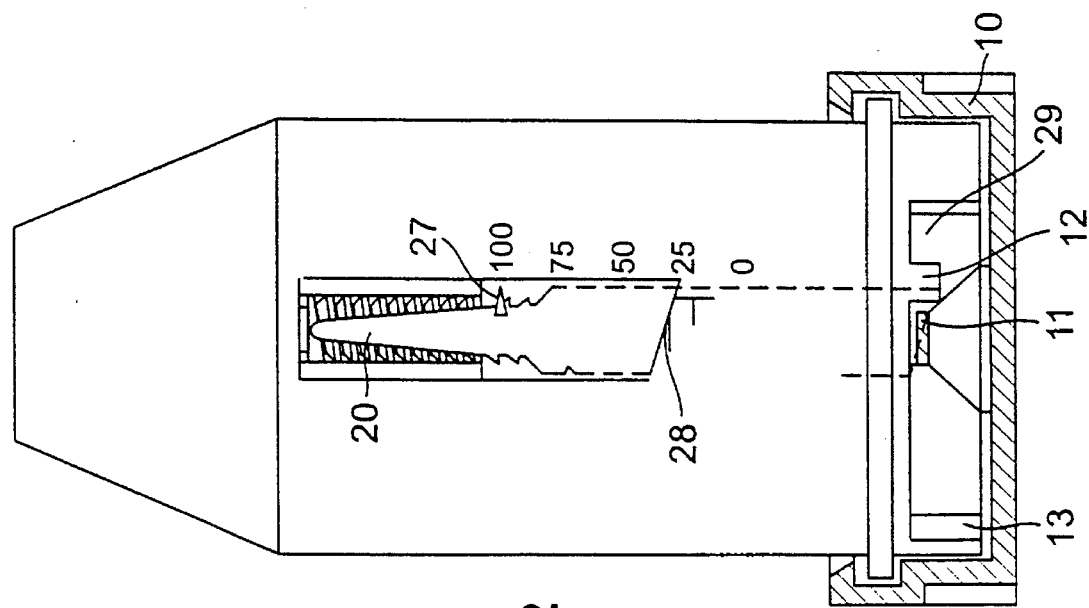
FIG. 2 shows a partly sectioned longitudinal view of the inhalator shown in FIG. 1.
Figure 1:
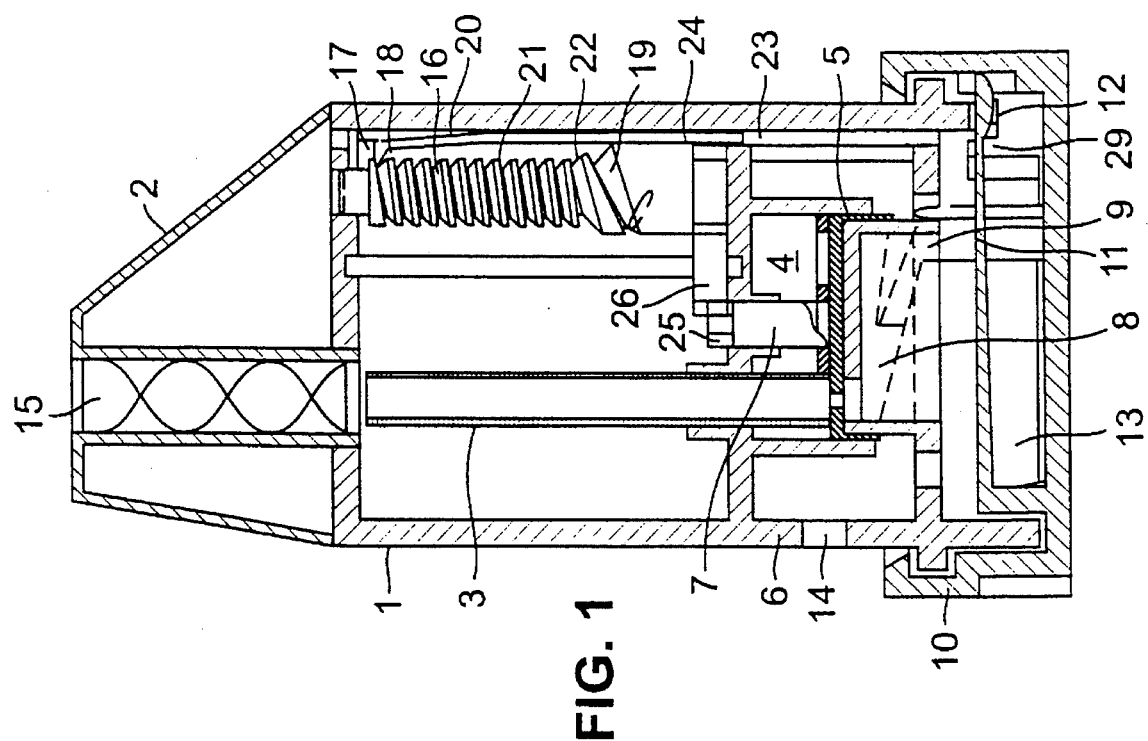
FIG. 1 shows a longitudinal section through a first embodiment of the inhalator.
Figure 3:
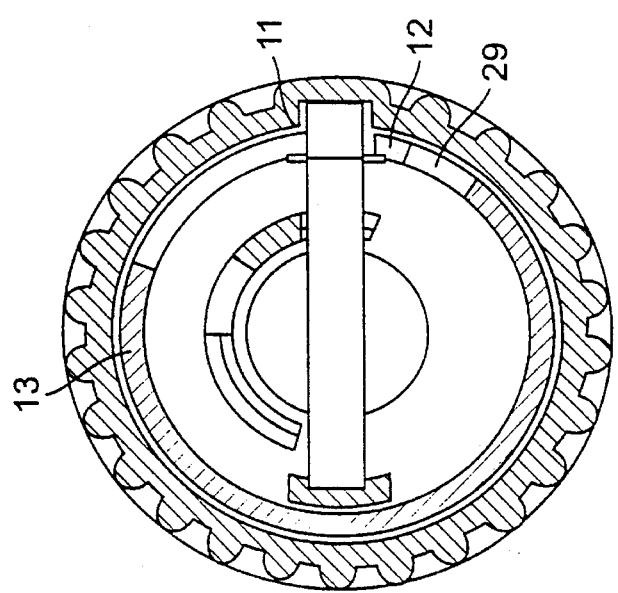
FIG. 3 shows a cross-section through the lower part of the inhalator in FIG. 1.

The invention will be illustrated below as adapted to a breath-actuated inhalator intended for administering a solid pharmacologically active compound in micronized form of the general kind described in U.S. Pat. No. 4,524,769. The expressions "upper", "lower" etc are only used below with reference to the orientation of the inhalator for instance FIG. 1 and are not to be construed as limiting. As shown in Figs 1–3, the inhalator in a first embodiment comprises a housing 1 on which a nozzle 2 is mounted. The housing contains a conduit 3 for conducting ambient air through the housing to the nozzle 2 when the patient inhales through the inhalator. The housing further contains a storage chamber 4 for the micronized compound. The compound is transferred to the air conduit 3 from the storage chamber by means of a rotatable disc or membrane 5 containing conical holes 6. The disc 5 is mounted on a shaft 7 which is journalled in the housing 1. The under side of the disc 5 is provided with a ratchet wheel 8 cooperating with a pawl 9 attached to a rotatable maneuvering wheel 10 journalled onto the bottom of the housing 1. The movement of the maneuvering wheel 10 relative to the housing 1 is limited by means of a lever 11, which is attached to the wheel 10, and two stops in the form of projections 12, 13 extending downwards from the housing. When the wheel 10 is rotated in one direction from one limit to the other, the ratchet wheel 8, and consequently also the disc 5, will be rotated a distance which is determined by the distance between the stops 12, 13. When the maneuvering wheel is rotated in the other direction the ratchet wheel 8 and the disc 5 will remain stationary. The holes 6 are located in such a way on the disc that there always will be one or several holes 6 which will be located (and consequently will be filled) in the storage chamber 4 at the same time as one or several filled holes 6 are located in the air conduit 3 in one end position of the maneuvering wheel 10. This means that one movement of the maneuvering wheel 10 from one limit position to the other and back will ensure that there will be one or several filled holes 6 in the air conduit 3. When the patient inhales through the nozzle 2, air will be sucked through an air intake 14, through the holes 6 in the air conduit 3 to the nozzle 2, thus entraining the micronized compound in the holes 6 into the respiratory tract of the patient. The nozzle 2 may contain a deaggregating means 15 deaggregating any agglomerations that for instance may have formed when the micronized compound is filled into the holes 6.

When the inhalator has been used, a movement of the maneuvering wheel 10 from one end position to the other and back will, as mentioned above, ensure that a new dose will be located in the air conduit 3.

The housing also contains an indicating device in the form of a screw 16 and a nut means 17. The screw comprises two main parts 18 and 19. The upper flanks 21 of the threads form an oblique angle with the longitudinal direction of the screw whereas the lower flanks 22 of the threads are more or less perpendicularly oriented relative to the longitudinal direction of the screw 16. The nut means is in the form of a tip 17 attached to a resilient arm 20 slideably supported in a guide 23 on the inner wall of the housing 1. In the initial position the major part of the arm 20 extends out from the guide 23. The under side of the tip 17 is oriented to be generally parallel to the upper flanks of the threads and the upper side of the tip 17 is oriented to be generally in parallel to the lower flank of the threads. This results in that the arm 20 and the tip 17 can be slid along the screw in the manner of a ratchet mechanism to any desired position along the upper part of the screw. The tip will however move downwards with the rotation of the screw from any such position. The upper part 18 of the screw 16 is generally cylindrical, whereas the lower part 19 is conical in shape. The pitch of the threads on the cylindrical part 18 of the screw 16 is much finer than the pitch of the threads on the conical part 19.

The upper part of the arm 20 is initially bent inwards, by which means the tip 17 is spring-biased towards the threads of the screw 16.

When the arm 20 moves downwards in the guide 23, an increasing length of the arm will be located in the guide and consequently be bent outwards and fixed against the wall of the housing 1, entailing that the arm will lose more and more of its resiliency, with the consequence that the tip 17 will be held more and more fixedly relative to the screw 16.

The lower end of the screw 16 is provided with cogs 24 which are engagement with cogs 25 on the shaft 7 by means of an intermediate cogwheel 26. A rotation of the disc 5 consequently will result in a rotation of the screw 16 entailing a downward movement of the arm 20. The outer side of the arm 20 is provided with a scale indicating the number of doses still remaining which is visible through a window in the housing provided with an index 27.

A visual indication that the supply of the compound is close to be exhausted can be obtained in that the window is designed with a length which is sufficient to allow the screw to be seen above the arm when the arm comes close to its lower end position. In this case the screw preferably should be made of brightly colored material to indicate exhaustion of available doses.

The lower end 28 of the arm 20 is oriented obliquely relative to the longitudinal direction of the inhalator. The guide 23 is located just before the stop 12 limiting the movement of the lever 11, as seen in the direction of movement of the lever 11 towards the stop 12. A cut out portion 29 in the lower edge of the wall of the housing 1 having a width corresponding to the width of the lever 11 is located adjacent the stop 12 after the stop 12.

Initially, directly after the manufacturing of the inhalator, the nut or tip 17 is located above the threads of the screw 16. By this means the function of the dosing disc and its associated mechanisms can be tested in conjunction with the manufacture of and before the filling of the inhalator without actuating the indicating means. When the device is filled, the tip 17 is pushed into engagement with the threads of the screw 16. If the full amount of micronized compound possible is to be filled into the storage chamber, the tip 17 is merely pushed downwards into engagement with the uppermost of the threads and the maximum number of doses will be visible in the window. Should it be desirable to fill a smaller amount of micronized powder (i.e. a smaller number of doses), the tip 17 is slid further downwards over the threads, a smaller number of doses then being indicated in the window. This movement of the tip 17 can be performed automatically by means of pins of different lengths which are inserted through a hole in the upper wall of the housing directly above the guide 23, this preferably in conjunction with the filling of the inhalator.

The arm 20 will move downwards at a constant rate in conjunction with the rotation of the disc 5 as long as the tip 17 is located on the upper part 18 of the screw 16. When the tip 17 reaches the conical part 19 of the screw, the downward movement of the tip will accelerate due to the much coarser pitch of the threads on this part and the lower end 28 of the arm 20 will move relatively fast into the path of the lever 11. At its lowest position (corresponding to an almost exhausted storage chamber), the lower end 28 of the arm 20 will function as a slideway for the resilient lever 11 which by this means is lifted over the stop 12 and snaps down into the cut out portion 29 behind the stop 12. The lever can be locked in either the loading or the dispensing position of the carrying means depending on the location of the cut out portion 29.

By this means the maneuvering wheel will be locked, giving a clear indication that the inhalator should not be used any more.

Figure 4:
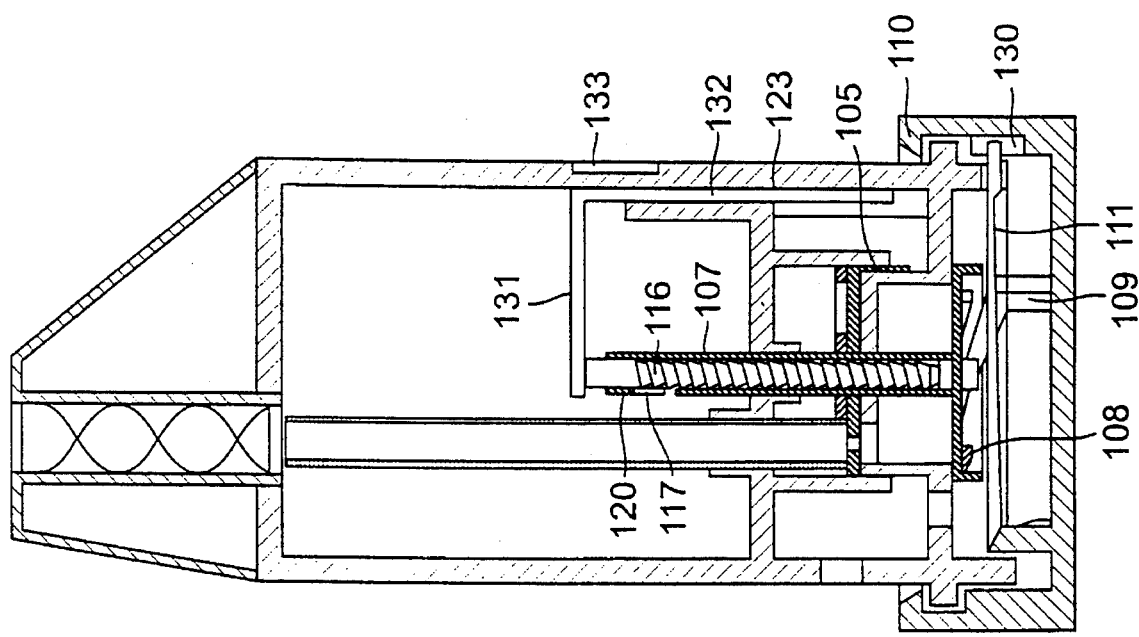
FIG. 4 shows a longitudinal section through a second embodiment of the inhalator.

An alternative embodiment of the inhalator is shown in FIG. 4. The reference signs for parts in FIG. 4 being similar to parts in FIGS. 1–3 differ from the reference signs relating to FIGS. 1–3 only in that they are numbered from 100 and upwards. Only the parts being necessary for the understanding of the differences between the two embodiments will be described in connection with FIG. 4.

In this embodiment the shaft 107 mounting the rotatable disc 105 is shaped as a hollow sleeve containing the screw 116. The threads on the screw 116 have the same general shape as the threads in the above embodiment although they may have the same pitch over the entire length of the screw. The screw 116 will be oriented upside down relative to the screw 16 in FIGS. 1–3, the sloping flanks of the threads will be facing downwards.

The arm 120 is shaped as a resilient tongue cut longitudinally in the wall of the sleeve 107 with the free end facing downwards and carrying the nut means in the form of a tip 117 projecting into the interior of the sleeve 107. The tip 117 has the general shape of the tip 17 in the above embodiment but is also turned upside down in relation to the tip 17. The pitch of the screw is chosen such that the screw will move downwards when the disc 105 is rotated by means of the ratchet mechanism 108, 109.

The screw thus can be pushed down to a desired position corresponding to a predetermined number of doses in a manner similar to the one of the nut means above. The screw will then move downwards from that position when the disc 105 is rotated.

The indicating means are in the form of a bar 132 carrying a scale showing the number of remaining doses through a window 133 and being slideable in a longitudinal guide 123 arranged on the inside of the wall of the housing 101. The bar 132 is rigidly connected to the screw 116 by means of an intermediate bar 131 and will consequently move with the longitudinal movements of the screw 116.

As described above, the screw 116 will move downwards for each rotational movement of the disc 105. When the contents of the storage chamber 104 is nearing exhaustion, the lower end of the screw 116 will engage the resilient lever 111 bending the lever downwards. Since the screw 116 engages the lever relatively close to the attachment point thereof, a relatively small movement of the screw will move the free end of the lever a comparatively large distance. In the end position of the screw, corresponding to an almost exhausted supply of micronized compound, the free end of the lever will be pushed down in an inner groove 130 in a wall portion of the maneuvering wheel 110, which means that the maneuvering wheel can be rotated freely without actuating the rotatable disc 105.

In this way again a clear indication is given that the inhalator is empty and consequently no longer should be used.

By the means described above, a dosage inhalator is obtained having indicating means which on one hand can be set to different numbers of doses of pharmacologically active compounds in a very simple way and which on the other hand gives a clear and unambiguous indication that the compound in the inhalator is exhausted and that the inhalator consequently no longer should be used. The constructive details enabling this are relatively simple and cheap to manufacture.

As mentioned above, the well-defined rotational reciprocal movement of the maneuvering means between two end positions indicate normal movement of said carrying means in connection with dispensing a unit dose into said conduit. The device according to the invention will drastically alter this regularity of the movement, either by locking the maneuvering means or by eliminating one or both of the two end positions of the maneuvering means.

POSSIBLE MODIFICATION OF THE INVENTION

It should be noted that the invention of course can be modified in many ways within the scope of the appended claims.

It should for instance be emphasized that, although the maneuvering means and the carrying means in the above preferred embodiments have been illustrated as being two separate parts, it of course also is conceivable to design the maneuvering means as an integral part of the carrying means, e.g. as a knurled portion of the carrying means extending through a slot in the housing.

In the above, preferred embodiments the scale is located on the housing and the index on the resilient arm 20. The scale can of course be located on the resilient arm and the index on the housing.

Another possible modification of the dosage inhalator according to the invention is to arrange the threads on the respective component in said screw and nut mechanism in a manner to allow them to be disengaged from each other in order to permit said translational movement.

We claim:

1. A dosage inhalator for dispensing to a patient a pharmacologically active compound suspended in a fluid comprising:

a housing, a nozzle extending from the housing and defining an outlet positioned for inhalation of the pharmacologically active compound by the patient and an inlet within said housing, storage means within said housing, for storing multiple doses of said active compound to be dispensed, a conduit in fluid communication between a conduit outlet at said inlet of said nozzle and conduit inlet at a region within said housing adjacent said storage chamber, carrying means having portions for carrying predetermined and reproducible unit doses of said active compound from said storage means to said conduit inlet, said carrying means being mounted for intermittent movement between said conduit inlet and said storage means to deliver one of said portions to said conduit whereby said unit dose of said active compound located at said portion can be dispensed through the conduit, maneuvering means for actuating said intermittent movement of said carrying means, said maneuvering means being positioned to be movable between first and second predetermined positions by a user of the inhalator, and means for disrupting the movement of said maneuvering means upon exhaustion of said active compound in said storage means, said means for disrupting being operably positioned with respect to said maneuvering means, wherein said carrying means is actuated by a ratchet mechanism including a spring-biased pawl, said maneuvering means includes a lever that is reciprocally displaceable between two distinct positions, and the movement of said ratchet mechanism is limited by said displacement of said lever.

2. A dosage inhalator of claim 1 wherein said means for disrupting the movement of said maneuvering means places said lever in a locked state upon exhaustion of said active compound in said storage means.

3. A dosage inhalator of claim 1 wherein said means for disrupting the movement of said maneuvering means causes said lever to be able to move freely beyond its predetermined first and second positions upon exhaustion of said active compound in said storage means.

4. A dosage inhalator of claim 1, or further comprising indicating means for indicating the number of doses remaining in said storage means or the number of doses used, said indicating means comprising a screw and nut mechanism including a nut that is positioned to be moved relative to a screw by said intermittent movement of said maneuvering means or said carrying means or both, the relative movement between screw and nut being used to actuate said means for disrupting the movement of said maneuvering means after a predetermined number of said intermittent movements.

5. A dosage inhalator for dispensing to a patient a pharmacologically active compound suspended in a fluid comprising:

a housing, a nozzle extending from the housing and defining an outlet positioned for inhalation of the pharmacologically active compound by the patient and an inlet within said housing, storage means within said housing, for storing multiple doses of said active compound to be dispensed, a conduit in fluid communication between a conduit outlet at said inlet of said nozzle and a conduit inlet at a region within said housing adjacent said storage chamber, carrying means having portions for carrying predetermined and reproducible unit doses of said active compound from said storage means to said conduit inlet, said carrying means being mounted for intermittent movement between said conduit inlet and said storage means to deliver one of said portions to said conduit whereby said unit dose of said active compound located at said portion can be dispensed into the conduit, maneuvering means for actuating said intermittent movement of said carrying means, said maneuvering means being positioned to be movable between first and second predetermined positions by a user of the inhalator, and means for indicating either the number of doses remaining in said storage means or the number of doses used, said indicating means comprising a screw and nut mechanism that includes a screw rotatable responsive to said intermittent movement of said carrying means and a nut displaceable laterally relative to said screw responsive to said rotation of said screw, wherein said maneuvering means includes a lever reciprocally displaceable between two distinct positions, said carrying means is actuated by a ratchet mechanism including a spring-biased pawl and the movement of said ratchet mechanism is limited by said displacement of said lever.

6. A dosage inhalator of claim 5 wherein said relative movement between said screw and said nut moves said lever to a position in which it is locked in place upon exhaustion of said active compound in said storage means.

7. A dosage inhalator of claim 5 wherein said relative movement between said screw and said nut moves said lever to a position in which it moves freely beyond its two distinct positions upon exhaustion of said active compound in said storage means.

8. A dosage inhalator of claim 5, wherein said screw and nut mechanism is capable of relative translational movement between the screw and the nut which produces a corresponding movement of said indicating means to a position indicating a predetermined number of doses present in said storage means.

9. A dosage inhalator of claim 5, wherein said nut is in the form of a resilient biased projection engaging the threads on the screw component, one of the flanks of said projection being more obliquely oriented relative to the longitudinal direction of the screw than the other flank to allow said projections to slide easily over the threads on the screw in one longitudinal direction but not in the opposite longitudinal direction in the manner of a ratchet mechanism.

10. A dosage inhalator of claim 9, wherein the flanks of the threads on the screw that engage said obliquely oriented flank on said projections slope conically to facilitate the sliding movement of said projection in said one longitudinal direction.

11. A dosage inhalator of claim 9 wherein said projection is located on a resilient arm or lever.

12. A dosage inhalator of claim 9, 10 or 11 wherein said nut includes a plurality of projections.

13. A dosage inhalator for dispensing to a patient a pharmacologically active compound suspended in a fluid comprising:

a housing, a nozzle extending from the housing and defining an outlet through which the pharmacologically active compound can be delivered to said patient and an inlet within said housing, a storage chamber within said housing containing multiple doses of said active compound to be dispensed through said nozzle, a conduit in fluid communication between a conduit outlet at said inlet of said nozzle and a conduit inlet at a region within said housing adjacent said storage chamber, a carrying member sized and positioned to deliver a predetermined unit dose of said active compound from the storage unit to the conduit inlet, said carrying member being actuated by a ratchet mechanism including a spring-biased pawl, a portion that is moveable by a user of the inhalator between a first position and a second position, said portion cooperating with said carrying member so that a movement of the portion between its first and second positions causes said carrying member to carry said unit dose from said storage chamber to a position at said conduit inlet in which said unit dose can be dispensed from the carrying member into the conduit, said portion including a lever reciprocally displaceable between two distinct positions, movement of said ratchet mechanism being limited by said displacement of said lever, and a disrupter responsive to the amount of said active compound remaining in said storage chamber by cooperating with said carrying member or said portion, said disrupter being adapted to disrupt movement of said outer portion upon exhaustion of said active compound in said storage chamber, said disrupter comprising an element moveable a predetermined distance each time said portion is moved between its first and second positions.

14. An inhalator of claim 13 wherein said disrupter renders said portion immovable upon exhaustion of said active compound in said storage chamber.

15. An inhalator of claim 13 wherein said carrying member includes a plurality of wells dimensioned to receive said predetermined dose and deliver said dose to said conduit.

16. An inhalator of claim 13 further including an indicator disposed and adapted to cooperate with said disrupter to indicate the number of doses in the storage chamber.

17. An inhalator of claim 16 wherein said indicator includes a screw and nut mechanism comprising a nut that is moved relative to a screw by said intermittent movement of said portion or said carrying member or both, the relative movement between screw and nut being used to actuate the disrupter after a predetermined number of said intermittent movements.

* * * * *